United States Patent [19]

Husslein et al.

[11] Patent Number: 4,515,985

[45] Date of Patent: May 7, 1985

[54] PREPARATION OF CHLORINATED PHENOXYALKANOIC ACIDS

[75] Inventors: Gerd Husslein, Bad Durkheim; Gerhard Hamprecht, Weinheim; Karl-Heinz Koenig, Frankenthal; Walter Boehm, Kirchheim; Manfred Gaeng, Bobenheim-Roxheim, all of Fed. Rep. of Germany

[73] Assignee: BASF Aktiengesellschaft, Fed. Rep. of Germany

[21] Appl. No.: 331,457

[22] Filed: Dec. 16, 1981

[30] Foreign Application Priority Data

Dec. 31, 1980 [DE] Fed. Rep. of Germany ....... 3049541

[51] Int. Cl.$^3$ ............................................. C07C 59/56
[52] U.S. Cl. .................................................... 562/472
[58] Field of Search ........................................ 562/472

[56] References Cited

U.S. PATENT DOCUMENTS 2,717,907  9/1955  Orwoll ................................ 562/472

FOREIGN PATENT DOCUMENTS 1027680  4/1958  Fed. Rep. of Germany .
 220978  10/1968  U.S.S.R. .

OTHER PUBLICATIONS

Zhurnal Prikladnoi Khimii, vol. 43 (1970), No. 12, pp. 2686–2692 (English Translation—pp. 2726–2730).

Primary Examiner—Paul J. Killos
Attorney, Agent, or Firm—Keil & Weinkauf

[57] ABSTRACT

A process for the preparation of 2,4-dichloro- or 2-methyl-4-chlorophenoxyacetic acid or α-2,4-dichloro- or α-2-methyl-4-chlorophenoxypropionic acid by reacting phenoxyacetic or 2-methylphenoxyacetic acid or α-phenoxypropionic or α-2-methylphenoxypropionic acid with chlorine in water, wherein phenoxyacetic acid or phenoxypropionic acid is precipitated from an aqueous solution thereof, chlorine gas is passed into the resulting suspension of phenoxyacetic or 2-methylphenoxyacetic acid or α-phenoxypropionic or α-2-methylphenoxypropionic acid in water at from 30° to 70° C. at a rate not exceeding the rate at which it is consumed in the suspension, until from 100 to 110% of the theoretically required amount of chlorine gas has been taken up by the suspension, and the 2,4-dichloro- or 2-methyl-4-chloro-phenoxyacetic acid or α-2,4-dichloro- or α-2-methyl-4-chloro-phenoxypropionic acid is isolated from the suspension.

2 Claims, No Drawings

PREPARATION OF CHLORINATED PHENOXYALKANOIC ACIDS

The present invention relates to an improved process for the preparation of 2,4-dichloro- or 2-methyl-4-chloro-phenoxyacetic acid or α-2,4-dichloro- or α-2-methyl-4-chloro-phenoxypropionic acid by reacting an aqueous suspension of phenoxyacetic or 2-methylphenoxy-acetic acid or α-phenoxypropionic or α-2-methylphenoxypropionic acid with chlorine gas.

Zh. Prikl. Khim. 43, 12 (1970), 2686–2692 (English translation ibid., 2726–2730) discloses that a yield of not more than 96% of theory of 2,4-dichlorophenoxyacetic acid (determined as the ester by gas chromatography) is obtained when phenoxyacetic acid is chlorinated with chlorine gas on a laboratory scale at 75° C. in water for from 4 to 6 hours. Industrial production of this substance by the process described has the following disadvantages:

1. Liquefied chlorine is used.
2. Melts of phenoxyacetic acid in water which are difficult to stir and to chlorinate are formed at the reaction temperature.
3. The space/time yield is too low because the chlorination proceeds too slowly and at too high a dilution.
4. Side reactions reduce the product quality; for example, the product has the unpleasant odor of 2,4-dichlorophenol as a result of acidic hydrolysis of the starting material and the end product.
5. Losses of chlorine during the reaction, ie. free chlorine gas in the off-gas, complicate purification of the off-gas.

Russian Pat. No. 220,978 discloses a process in which a chlorination temperature of from 60° to 65° C. is maintained during the reaction, the starting material is used in the form of a fine suspension (particle diameter: 0.5 mm) and the reaction is carried out in the presence of a large quantity of water (about 1 mole of phenoxyacetic acid per 300 moles of water). The purity of the end product from this process is not more than 80%, which is completely unsatisfactory in industry.

We have found that 2,4-dichloro- or 2-methyl-4-chloro-phenoxyacetic acid or α-2,4-dichloro- or α-2-methyl-4-chloro-phenoxypropionic acid is obtained in a yield of not less than 96% of theory and a purity of not less than 97% when phenoxyacetic or 2-methylphenoxyacetic acid or α-phenoxypropionic or α-2-methylphenoxypropionic acid is precipitated from an aqueous solution thereof, chlorine gas is passed into the resulting suspension of phenoxyacetic or 2-methylphenoxyacetic acid or α-phenoxypropionic or α-2-methylphenoxypropionic acid in water at from 30° to 70° C. at a rate not exceeding the rate at which it is consumed in the suspension, until from 100 to 110% of the theoretically required amount of chlorine gas has been taken up by the suspension, and the 2,4-dichloro- or 2-methyl-4-chloro-phenoxyacetic acid or α-2,4-dichloro- or α-2-methyl-4-chloro-phenoxypropionic acid is isolated from the suspension.

The phenoxyacetic or 2-methylphenoxyacetic acid or α-phenoxypropionic or α-2-methylphenoxypropionic acid can be precipitated from solution by, for example, adding acid or by passing in chlorine gas. In the former case, for example, hydrochloric acid is added to the aqueous solution until precipitation occurs. The introduction of chlorine gas is effected at a rate not exceeding that at which it is taken up by the suspension and consumed in the reaction. Advantageously, the chlorine gas is allowed to come into contact with the suspension for as long as possible, for example by stirring the suspension vigorously or by the chlorine having to penetrate a thick layer of the suspension.

For the purposes of the invention, a solution of phenoxyacetic or 2-methylphenoxyacetic acid or α-phenoxypropionic or α-2-methylphenoxypropionic acid in water is a solution either of the acid itself or of its alkali metal salts, for example the sodium salts or potassium salts or mixtures thereof.

The end product can be isolated from the reaction mixture by, for example, filtration.

An aqueous solution of phenoxyacetic or 2-methylphenoxyacetic acid or α-phenoxypropionic or α-2-methylphenoxypropionic acid, which has been obtained by reacting phenol or 2-methylphenol or an alkali metal salt thereof with chloroacetic acid or α-chloropropionic acid in an organic solvent and extracting the resulting phenoxyacetic or 2-methylphenoxyacetic acid or α-phenoxypropionic or α-2-methylphenoxypropionic acid from the organic solvent with water, can advantageously be used in the reaction. The substantial losses, for example of phenoxyacetic acid, occurring in the conventional processes as a result of using solid phenoxyacetic acid which has been isolated from its preparation solution are thereby avoided.

It is suprising that a high rate of reaction, leading to a product of high purity (not less than 97%), is achieved at the low temperatures and high starting material concentrations (about 1 mole of phenoxyacetic acid or α-phenoxypropionic acid in from 20 to 40 moles of water) used in the process according to the invention. It is therefore not necessary to prepare a fine suspension of the starting material of a particular particle size, as described in Russian Pat. No. 220,978, for example by milling the solid starting material. Thus, although milling is not employed, the concentration of the starting material in the process according to the invention can be increased 10-fold compared to that in the conventional process.

The reaction time in the process according to the invention is shortened to less than half that in the conventional processes as a result of adjusting the addition of chlorine gas to the rate of reaction and of precipitating the phenoxyacetic or 2-methylphenoxyacetic acid or α-phenoxypropionic or α-2-methylphenoxypropionic acid from aqueous solution. An increase in the residence time of the chlorine gas in the suspension contributes to this shortening. Since the chlorine reacts completely when passed into the reaction mixture, the end point of the reaction (appearance of free chlorine in the off-gas) is accurately recorded and loss of chlorine is avoided. Environmental pollution by the off-gas (hydrogen chloride) from the reaction can therefore be avoided by simple measures, for example by absorbing the off-gas in water, whereupon useful hydrochloric acid is again formed. Only very long reaction times (lowspace/time yield) and a large excess of chlorine give even approximately the yield achieved in Zh. Prikl. Khim. (see above) under the conditions described therein. The process according to the invention can be carried out batchwise or continuously.

The sharp rise in the chlorine content of the off-gas can be used to establish the end of the reaction. Dispersants, for example sodium lignin-sulfonate, can additionally be used to increase the rate of reaction further.

The phenoxyacetic or 2-methylphenoxyacetic acid solution or α-phenoxypropionic or α-2-methylphenoxypropionic acid solution used as the starting material can be prepared, for example, by reacting phenol or 2-methylphenol with chloroacetic acid or α-chloropropionic acid in an alkaline medium. In a particularly advantageous procedure, chloroacetic acid or α-chloropropionic acid, if desired in aqueous solution, and concentrated aqueous alkali metal hydroxide solution, for example 50% strength sodium hydroxide solution, are separately and simultaneously added dropwise to a boiling solution of phenol or 2-methylphenol in an organic liquid which forms an azeotropic mixture with water, for example toluene or xylene, the water present and that formed in the reaction being removed from the system. For example, after the reaction, a layer of water is introduced below the organic phase and, after the phases have been separated and the aqueous solution has been acidified, the chlorination is carried out continuously or batchwise, under atmospheric or superatmospheric pressure and with or without a reaction accelerator, as described above. After the required amount of chlorine gas has been passed in, the mixture is advantageously stirred at the reaction temperature for a further 15–30 minutes and is then filtered with suction.

EXAMPLE 1

A solution of 98 parts (by weight) of chloroacetic acid in 50 parts of water and a solution of 88 parts of sodium hydroxide in 90 parts of water are separately and simultaneously added dropwise to a boiling solution of 94 parts of phenol in 500 parts of xylene, in the course of 60 minutes. The mixture is then stirred at 140° C. for 30 minutes, 500 parts of water are added, with stirring, and the aqueous phase is separated off. Concentrated hydrochloric acid is then added to the aqueous phase, with vigorous stirring, until the pH is 3, and 150 parts (by weight) of chlorine gas are then passed in at 50° C. in the course of 90 minutes in a manner such that no chlorine appears in the off-gas. Stirring is continued at 50° C. for 15 minutes and the precipitate is filtered off with suction and washed with water. After drying, 216 parts (98% of theory, based on phenol employed) of 98% pure 2,4-dichlorophenoxyacetic acid of melting point 138°–140° C. are obtained.

EXAMPLE 2

267 parts of 50% strength (by weight) potassium hydroxide solution are added to a mixture of 211.5 parts of phenol and 225 parts of water, and 370 parts of 64% strength aqueous chloroacetic acid solution are then added dropwise under reflux (105°–108° C.) in the course of 60 minutes, until the pH of the solution has fallen to 10; the pH is then maintained by simultaneous and separate addition of chloroacetic acid and addition of 190 parts of 50% strength aqueous sodium hydroxide solution. The mixture is stirred under reflux for a further 60 minutes, 700 parts of water are then added and the mixture is acidified to pH 4 with concentrated hydrochloric acid, with vigorous stirring. 173 parts of chlorine gas are passed in at from 40° to 50° C. in the course of 100 minutes in a manner such that no free chlorine appears in the off-gas. Stirring is continued for a further 30 minutes at 50° C., and the precipitate is filtered off with suction and washed salt-free with water to give, after drying, 487 parts (98% of theory, based on phenol employed) of 97% pure 2,4-dichlorophenoxyacetic acid of melting point 137°–139° C.

EXAMPLE 3

A solution of 94 parts of chloroacetic acid in 60 parts of water in a mixture of 66 parts of 50% strength aqueous NaOH solution and 93 parts of 50% strength aqueous KOH solution are separately and simultaneously added dropwise to a mixture of 134.5 parts of phenol, 33 parts of 50% strength (by weight) aqueous NaOH solution, 46 parts of 50% strength aqueous KOH solution and 50 parts of water at from 105° to 108° C. in the course of two hours. The mixture is then stirred for 30 minutes at 105° C., 900 parts of water are added and the reaction mixture is extracted twice with 150 parts of methyl tert.-butyl ether each time. 57 parts of chlorine are passed into the aqueous phase at 50° C. in the course of 5 minutes, the organic phase is allowed to settle, the aqueous phase is separated off and 1,000 parts of fresh water at 60° C. are added to the organic phase. The aqueous phases are combined, 85 parts of chlorine gas are passed in at 55° C. in the course of 15 minutes, the mixture is left to react for 15 minutes and the product is filtered off with suction at 35° C. Yield: 415 parts (94% of theory) of 2,4-dichlorophenoxyacetic acid of melting point 138° to 141° C. and 97% purity.

EXAMPLE 4

530 parts of 50% strength aqueous NaOH solution and 362 parts of 90% strength α-chloropropionic acid are separately and simultaneously added dropwise to a boiling solution of 338.4 parts of phenol in 2,000 parts of toluene in the course of two hours, the water being removed from the system. The mixture is then stirred for a further hour at 110° C., 2,000 parts of water are added, the organic phase is separated off and the aqueous phase is extracted twice at pH 6 with 500 parts of toluene each time. After passing steam through for a short time, 430 parts of chlorine gas are passed into the aqueous phase at 55° C. in the course of 35 minutes, and the reaction product is then filtered off. Yield: 652.2 parts (92% of theory) of α-2,4-dichlorophenoxypropionic acid of melting point 116°–118° C. and 98.5% purity.

EXAMPLE 5

180 parts of chlorine gas are passed into a mixture of 415 parts of 2-methylphenoxyacetic acid and 2,500 parts of water at 60° C. in the course of 50 minutes. After filtering off the precipitate with suction and washing it with water, 481.2 parts (96% of theory) of 2-methyl-4-chlorophenoxyacetic acid of melting point 116°–119° C. and 96% purity are obtained.

We claim:

1. A process for the preparation of 2,4-dichloro- or 2-methyl-4-chlorophenoxyacetic acid or α-2,4-dichloro- or α-2-methyl-4-chlorophenoxypropionic acid by reacting phenoxyacetic or 2-methylphenoxyacetic acid or α-phenoxypropionic or α-2-methylphenoxypropionic acid with chlorine in water, wherein phenoxyacetic or 2-methylphenoxyacetic acid or α-phenoxypropionic or α-2-methyl-phenoxypropionic acid is precipitated from an aqueous solution thereof, chlorine gas is passed into the resulting suspension of the acid in water at from 30° to 70° C. at a rate not exceeding the rate at which it is consumed in the suspension, until from 100 to 110% of the theoretically required amount of chlorine gas has been taken up by the suspension, and the 2,4-dichloro- or 2-methyl-4-chlorophenoxyacetic acid or α-2,4-dichloro- or α-2- methyl-4-chloro-phenoxypropionic acid is isolated from the suspension.

2. The process of claim 1, wherein an aqueous solution of phenoxyacetic or 2-methylphenoxyacetic acid or α-phenoxypropionic or α-2-methylphenoxypropionic acid, which has been obtained by reacting phenol or 2-methylphenol or an alkali metal salt thereof with chloroacetic acid or α-chloropropionic acid or an alkali metal salt thereof in water or an organic solvent and extracting the resulting phenoxyacetic or 2-methylphenoxyacetic acid or α-phenoxypropionic or α-2-methylphenoxypropionic acid from the organic solvent with water, is used as the starting material.

* * * * *